United States Patent [19]

Molina

[11] 4,054,535
[45] * Oct. 18, 1977

[54] VARIABLE SENSITIVITY WATER WASHABLE DYE PENETRANT

[75] Inventor: Orlando G. Molina, Westminster, Calif.

[73] Assignee: Rockwell International Corporation, El Segundo, Calif.

[ * ] Notice: The portion of the term of this patent subsequent to Oct. 28, 1992, has been disclaimed.

[21] Appl. No.: 590,177

[22] Filed: June 25, 1975

Related U.S. Application Data

[63] Continuation-in-part of Ser. No. 444,432, Feb. 21, 1974, Pat. No. 3,915,885, Ser. No. 444,433, Feb. 21, 1974, Pat. No. 3,915,886, Ser. No. 535,262, Dec. 23, 1974, Pat. No. 3,981,185, and Ser. No. 521,730, Nov. 7, 1974, Pat. No. 3,939,092.

[51] Int. Cl.$^2$ .................... C09K 11/06; G01N 19/08; G01N 21/16
[52] U.S. Cl. .................... 252/301.19; 23/230 R; 73/104; 250/302; 252/408
[58] Field of Search .................... 252/301.19, 408; 23/230 R; 73/104; 250/302

[56] References Cited

U.S. PATENT DOCUMENTS 3,915,885 10/1975 Molina ................ 252/301.2 P
3,915,886 10/1975 Molina ................ 252/301.2 P Primary Examiner—John H. Mack
Assistant Examiner—Aaron Weisstuch
Attorney, Agent, or Firm—Charles T. Silberberg; L. Lee Humphries

[57] ABSTRACT

Variable sensitivity biodegradable water washable dye penetrant compositions for use in non-destructive dye penetrant inspection of parts, such compositions basically consisting essentially of an organic dye, preferably a fluorescent dye, and a carrier or solvent for said dye, in the form of a surfactant comprised of certain straight chain, primary, aliphatic oxyalkylated alcohols, particularly biodegradable surfactants comprised of the nonionic condensation products of linear primary aliphatic alcohols having from 10 to 18 carbon atoms, with ethylene oxide and propylene oxide, preferably in the form of a mixture thereof, such as the material marketed as Plurafac A-24, or in the form of certain ethoxylated secondary alcohols, particularly the biodegradable nonionic surfactants comprised of ethoxylates of a mixture of secondary alcohols having linear alkyl chains of from 11 to 15 carbon atoms, such as Tergitol 15-S-5 or Tergitol 15-S-9, the variations in sensitivity being provided by the addition to the above basic composition of controlled amounts of the above surfactant component, the resulting compositions all having substantially the same water washability.

In the method of application of the dye penetrant composition of the invention, such composition is applied to the surface of an object containing cracks and flaws, water is applied to the surface of the object to remove excess dye penetrant composition from the surface without removing such penetrant from the cracks and defects, and with or without a developer, the surface of the object is viewed under suitable lighting conditions, e.g. ultraviolet or black light when the dye in the penetrant is a fluorescent dye, to locate any cracks or defects in the surface of the body as indicated by colored traces from the dye penetrant remaining in the cracks and flaws.

10 Claims, No Drawings

VARIABLE SENSITIVITY WATER WASHABLE DYE PENETRANT

This application is a continuation-in-part of my co-pending applications Ser. Nos. 444,432 and 444,433, both filed Feb. 21, 1974, now U.S. Pat. Nos. 3,915,885 and 3,915,886 respectively; 521,730, filed Nov. 7, 1974, now U.S. Pat. No. 3,939,092; and 535,262, filed Dec. 23, 1974, now U.S. Pat. No. 3,981,185.

BACKGROUND OF THE INVENTION

This invention relates to variable sensitivity biodegradable water washable dye penetrant compositions and method for non-destructively testing material specimens to locate and identify surface voids, cracks or defects. The invention is especially concerned with variable sensitivity dye penetrant compositions having the above characteristics, and wherein the sensitivity is controlled simply by incorporation into a basic composition, of additional amounts of the dye vehicle or carrier component of the basic dye penetrant composition, essentially without changing the water washability of the compositions, and employing as vehicle or carrier certain biodegradable nonionic surfactants in the form of certain oxyalkylated alcohols, and mixtures thereof; to a method for preparing such variable sensitivity dye penetrant compositions; and to a method of utilizing such variable sensitivity dye penetrant compositions for non-destructive testing of parts having cracks or defects varying in size from microcracks to gross cracks.

In known penetrant inspection methods for rapid location and evaluation of surface flaws or cracks in test bodies or parts, a dye penetrant composition, preferably containing a fluorescent dye, and which will penetrate the openings of the surface cracks or flaws in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions, such as invisible fluorescigenous light, and the location of the surface flaws is revealed by the emission of visible fluorescent light by the penetrant dye which was retained in the cracks or flaws after the penetrant composition was removed from the surface of the part.

For best efficiency, particularly for the detection and location of minute surface cracks and flaws, as well as intermediate size and gross cracks, dye penetrant compositions are required having varying sensitivity ranging from very high sensitivity, down to medium and low sensitivity.

In addition, it is highly desirable that the various dye penetrant solutions of variable sensitivity be easily formulated and contain a minimum of vehicle or carrier components, and particularly that all of such variable sensitivity dye penetrant compositions have easy water washability from part surfaces without the necessity for carefully balancing a variety of the liquid components which are usually present in prior art dye penetrant solutions, in order to obtain such variable sensitivity and washability control.

Prior art dye penetrant compositions generally consist of various ingredients including in addition to dyes, combinations of solvents such as primary and secondary solvents, wetting agents, often employed in combination, and extenders for controlling the washability of the dye penetrant composition and maintaining its stability in solution. When employing such prior art dye penetrants, in order to obtain different penetrant sensitivities, each formulation of a desired sensitivity requires careful mixing and balancing of the above components. In addition, however, such compositions of varying sensitivity containing the above multiple components generally vary in washability, due to the varying proportions particularly of water insoluble components in such composition.

Thus, in my application Ser. No. 16,804, filed Mar. 5, 1970, abandoned in favor of continuation application Ser. No. 333,494, filed Feb. 20, 1973, now abandoned, there is disclosed production of graded sensitivity dye penetrants employing combinations of dye carriers such as N-methyl-2-pyrrolidone and isobutyl heptyl ketone, together with combinations of soluble and insoluble wetting agents, and wherein a controlled and graded degree of sensitivity for crack detecting is obtained by mixing dye penetrant compositions of these types, each containing different proportions of components, in order to obtain a dye penetrant of a desired sensitivity. Thus, according to such disclosure, two extreme penetrant compositions, that is one of high and the other of low sensitivity are mixed to obtain dry penetrant compositions of intermediate sensitivities. This concept is based on the nature of the dye penetrants employed, which have substantially the same amount of dye for both of the extreme sensitivity formulations noted above, but the resulting compositions of varying sensitivity differ in water solubility and washability characteristics for each formulation.

An additional criterion has recently developed also with respect to dye penetrant solutions and compositions. Generally, dye penetrant solutions presently being used and containing solvents and wetting agents present a disposal problem in that they are substantially non-biodegradable, that is, they are very difficult to decompose by bacteria in sewage disposal plants. Hence, the necessity for the development of dye penetrant solutions and compositions which are biodegradable, that is which employ dye solvents and carriers which are biodegradable, and are readily available despite the petrochemical shortage, has attained considerable importance.

In my above U.S. Pat. Nos. 3,915,885 and 3,915,886 there are disclosed novel dye penetrants which have improved washability and sensitivity characteristics, and which are biodegradable, containing as the vehicle for the dye, certain biodegradable nonionic oxyalkylated alcohols.

Accordingly, an object of the present invention is the provision of variable sensitivity biodegradable water washable dye penetrant compositions which are based on a simple formulation comprised of an essentially single or sole vehicle or carrier for the dye in the form of a biodegradable nonionic surfactant, and which are heat stable, and are essentially non-flammable and non-toxic, and which do not require the use of volatile primary and secondary solvents and couplants, or mixtures thereof. A particular object of the invention is to provide dye penetrant compositions of the above noted type, and wherein the sensitivity of the dye penetrant compositions can be easily controlled simply by addition of predetermined amounts of the above surfactant to the basic dye penetrant, while essentially maintaining the same good washability characteristics for all of the compositions thus obtained, but with varying sensitivity. Still further objects are the provision of procedure for preparing such variable sensitivity water washable and heat stable biodegradable dye penetrant compositions, and procedure employing such compositions for inspection of cracks, flaws and metallurgical conditions in structural components.

DESCRIPTION OF THE INVENTION

According to the present invention it has been found that biodegradable dye penetrant compositions having almost an infinitely variable degree of penetrant sensitivity can be produced utilizing as basic dye penetrant composition a composition containing as a solvent or carrier for the dye, e.g. fluorescent dye, a surfactant in the form of certain biodegradable nonionic surfactants comprised of certain oxyalkylated linear alcohols, of the types disclosed in my above U.S. Pat. Nos. 3,915,885 and 3,915,886, separately or in admixture. In effect, such surfactant functions as a single liquid vehicle or carrier for the dye. Upon incorporation of varying predetermined proportions of the above surfactant into the above basic dye penetrant composition, dye penetrant compositions can be formulated which range in sensitivity from very high sensitivity to medium or low sensitivity, but without changing the solubility or water washability of the various resulting dye penetrant compositions.

Thus, in contrast to the disclosure of my above application Ser. Nos. 16,804 and 333,494, now abandoned, which utilize a plurality, e.g. two, previously mixed and complex dye penetrant compositions of extreme sensitivities and having different washabilities for producing dye penetrant compositions of intermediate or graded sensitivities, the present invention employs a simple, essentially sole liquid component or dye carrier containing a predetermined amount of dye, either fluorescent or non-fluorescent dye, and having a high degree of sensitivity, and whose sensitivity can be reduced in a controlled manner by adding additional predetermined amounts of the same liquid carrier component as in the basic dye penetrant composition, to affect only the ability of the dye remaining in the cracks and flaws to be seen or detected. Thus, the addition of progressively increasing amounts of the above nonionic surfactant to the basic dye penetrant composition containing such surfactant progressively desensitizes the basic dye penetrant composition so that dye penetrant compositions can be formulated which vary from very high sensitivity to low sensitivity depending upon the amount of additive surfactant incorporated. However, all of the resulting dye penetrant compositions of varying sensitivity thus formulated will possess practically the same good solubility and washability as the initial or basic dye penetrant composition, but varying only in sensitivity or "seeability."

Briefly then, the invention provides a variable sensitivity water washable dye penetrant composition which comprises a basic dye penetrant composition comprising (1) a biodegradable nonionic oxyalkylated alcohol surfactant as defined below, and (2) a small amount of a dye soluble in said surfactant, such basic dye penetrant composition containing a predetermined additional amount of said nonionic surfactant sufficient to decrease the sensitivity of said basic composition, the resulting desensitized dye penetrant composition having substantially the same washability as said basic composition.

The additional predetermined amounts of nonionic surfactant added to the basic dye penetrant composition can range from an amount which varies the sensitivity of the resulting dye penetrant composition from very high sensitivity to low sensitivity.

It is accordingly seen that the present invention provides a simple and effective concept for producing variable sensitivity biodegradable and water washable dye penetrant compositions involving essentially only the addition of predetermined amounts of vehicle or carrier component to the basic dye penetrant composition, without affecting the water washability characteristics of the initial or basic dye penetrant composition.

The nonionic biodegradable solvent or carrier employed essentially as the sole vehicle or carrier for the dye of the dye penetrant compositions according to the invention can be alkylene oxide condensation products prepared by the reaction of an organic compound having a reactive hydrogen atom, such as an aliphatic alcohol, with ethylene oxide, propylene oxide, or mixtures thereof. More particularly, one class of such nonionic solvents or carriers can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One class of nonionic carriers within the broad class of materials defined above is a cogeneric mixture of compounds represented by the formula:

wherein:
R is an essentially linear alkyl group having from 10 to 18 carbon atoms, with the proviso that at least 70 weight percent of said compounds in said mixture have an R of from 12 to 16 carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formula, ranges from 12 to 18 carbon atoms, and the total number of ethylene oxide and propylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols which are operable include decyl alcohol, undecyl alcohol, lauryl alcohol, tridecyl alcohol, tetra-decyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The above nonionic biodegradable surfactants employed as carrier or vehicle for the dye of the penetrant solution according to the invention, are prepared by condensing an alcohol or mixture of alcohols, as described above, with a mixture of ethylene oxide and propylene oxide, in the presence of an alkaline catalyst, such as potassium hydroxide. The oxide mixture may be added to the alcohol in one continuous step or it may be added in several steps. The products thus produced possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include, for example, that class of surfactants which are marketed as "Plurafac" surfactants "RA-40" grades.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12.75, and the number of propylene oxide groups in such mixture ranges from 1.7 to 7.0, the oxyethylene to oxypropylene ratio in such mixtures being from 1.8:1 to 2.2:1. Such cogeneric mixtures can be prepared in two steps, the first step being condensation of an alcohol mixture and ethylene oxide in the presence of an alkaline condensing agent or catalyst, to form an ethoxylated product, followed by condensing the resulting ethoxylated product with propylene oxide. There can be employed in such reaction a mixture of straight chain aliphatic alcohols having from 8 to 20 carbon atoms in the aliphatic chain. This cogeneric mixture of condensation products and the method of their preparation are disclosed in U.S. Pat. No. 3,340,309, and such disclosure is also incorporated herein by reference. The nonionic oxyalkylated alcohols marketed as the "RA-20" grades of "Plurafac", are believed representative of the class of surface active agents disclosed in the latter patent.

Various other "Plurafac" grades which are marketed and are believed to be generally within the above-described classes of oxyalkylated alcohol surfactants are those designated RA-43, A-24, A-25, B-25-5, B-26 and D-25.

A class of particularly preferred nonionic biodegradable solvents or carriers which can be employed as substantially the sole vehicle for the dye of the dye penetrant compositions according to the present invention are ethoxylates of a mixture of linear secondary aliphatic alcohols, with the hydroxy groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred clas of nonionic biodegradable surfactant employed as carrier for the dye penetrant of the invention is a mixture of compounds which can be represented by the formula:

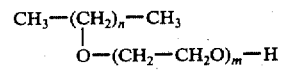

wherein $n$ is in the range from 9 to 13, and $m$ is an average of 3 to 12.

Although preferably each of the immediately above-defined surfactants is formed of a mixture of two or more linear alkyl hydrophobic chains ranging from $C_{11}$ to $C_{15}$ as noted below, the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a

group. Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively, as:

| Tergitol | 15-S-3 |
|----------|--------|
| "        | 15-S-5 |
| "        | 15-S-7 |
| "        | 15-S-9 |
| "        | 15-S-12 |

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. However, Tergitol 15-S-3, when employed in suitable proportions in combination with the other water washable and water soluble Tergitols such as Tergitol 15-S-5 and/or Tergitol 15-S-9, also results in water soluble and water washable dye pentrants. Other mixtures of these materials also can be employed, a particularly preferred vehicle for the basic dye penetrant composition being a mixture of Tergitols 15-S-5 and 15S-9, such mixtures being added to the basic dye penetrant composition for varying the sensitivity thereof while producing water washable dye penetrants, according to the invention.

The above preferred class of nonionic biodegradable surfactants employed as carrier or vehicle for the dye of the penetrant solution according to the invention, are prepared by reacting an alcohol or mixture of alcohols, as described above, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Another process for preparing the above preferred nonionic surfactants in the form of ethoxylates of linear secondary aliphatic alcohols, is described in U.S. Pat. No. 2,870,220.

Any suitable dye generally employed in dye penetrant compositions can be incorporated into the nonionic oxyalkylated alcohol surfactants described above for producing the dye penetrant compositions employed in the invention process. Preferably, however, a fluorescent dye is employed for this purpose. The oxyalkylated surfactant vehicle for the dye is compatible therewith and has the ability to dissolve either small or relatively large amounts of the dye and to hold a high concentration of dye in solution while providing good resolution and clarity of the dye trace in the cracks and flaws.

As previously noted, the dye penetrant solutions employed according to the invention preferably contain a fluorescent dye. Various types of fluorescent dyes can be employed including for example the dye marketed as Fluorol 7Ga, Morton Yellow "G", as well as other fluorescent dyes such as those marketed as Calcofluor Yellow, Azosol Brilliant Yellow 6GF; Rhodanine B, Rhodanine 6 GDN, Calcofluor White RW, Blancophor White AW, Auramine and Eosine G, and water soluble fluorescent dyes such as Blancophor FFG.

The dye penetrant composition employed according to the invention alternatively can contain non-fluorescent or daylight type dyes such as azo type dyes, e.g., xylenaezo-beta-naphthol, Mefford No. 322 dye, believed to be o-toluene-azoxyleneazo-beta-naphthol, and the azo dyes marketed as Oil Red "O" and Sudan Red. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

The amount of dye which is incorporated into the oxyalkylated alcohol surfactant or carrier to produce the basic dye penetrant composition can range from about 0.1 to 15, preferably about 0.5 to about 10, parts of the dye, or mixtures thereof, per 100 parts of the oxyalkylated alcohol surfactant, by weight. In preparing such dye penetrant composition, the dye is simply added to the oxyalkylated alcohol carrier, in the desired proportion to produce the basic dye penetrant composition.

Typical liquid basic dye penetrant compositions which can be employed according to the invention to obtain dye penetrant compositions of varying sensitivity are as follows:

TABLE 1

| COMPONENTS | Liquid Compositions (Parts by Weight) | | | | | | | | |
|---|---|---|---|---|---|---|---|---|---|
| | A | B | C | D | E | F | G | H | I |
| Tergitol 15-S-3 | — | — | — | — | 25 | — | — | — | — |
| Tergitol 15-S-5 | 100 | — | 75 | — | 75 | — | 75 | 75 | 75 |
| Tergitol 15-S-9 | — | — | 25 | — | — | 100 | 25 | 25 | 25 |
| Plurafac A-24 | — | 100 | — | — | — | — | — | — | — |
| Plurafac RA-43 | — | — | — | 100 | — | — | — | — | — |
| Calcofluor White RW | 5.0 | 5.0 | 5.0 | 5.0 | 2.5 | 2.5 | 2.5 | 1.25 | 0.625 |
| Fluorol 7GA | 1.5 | 1.5 | 1.5 | 1.5 | 0.75 | 0.75 | 0.75 | 0.37 | 0.19 |

The amount of additional nonionic oxyalkylated surfactant carrier or vehicle component which is added to the basic dye penetrant composition, as illustrated by compositions A through I of Table 1 above, to vary or control the sensitivity of the resulting dye penetrant composition, to obtain desensitized dye penetrant compositions ranging from very high sensitivity to low sensitivity, can vary over a wide range, for example from about 0.5 to about 100, usually about 1 to about 75, parts of the nonionic surfactant vehicle additive, to 10 parts, by volume, of basic dye penetrant composition. Thus, for example, employing the basic dye penetrant composition C of Table 1 above, utilizing a combination of Tergitol 15-S-5 and Tergitol 15-S-9 as surfactant vehicle for the dye, there can be added to such basic dye penetrant composition, a mixture of 75% Tergitol 15-S-5 and 25% Tergitol 15-S-9 as surfactant, in the proportions of such mixture noted in Table 2 below, to obtain dye penetrant compositions of varying sensitivity or desensitization, as noted in the last column to the right of Table 2 according to the invention.

TABLE 2

| No. | Dye Penetrant Composition C - (Parts by Volume) | Added Mixture of 75% Tergitol 15-S-5 and 25% Tergitol 15-S-9, by vol - (Parts by Volume) | Sensitivity Range |
|---|---|---|---|
| C | 10 | 0 | High Plus |
| 1 | 10 | 1 | |
| 2 | 10 | 2 | |
| 3 | 10 | 3 | |
| 4 | 10 | 4 | |
| 5 | 10 | 5 | High |
| 6 | 10 | 6 | |
| 7 | 10 | 7 | |
| 8 | 10 | 8 | |
| 9 | 10 | 9 | |
| 10 | 10 | 10 | |
| 11 | 10 | 12 | |
| 12 | 10 | 15 | |
| 13 | 10 | 20 | |
| 14 | 10 | 30 | Medium |
| 15 | 10 | 40 | |
| 16 | 10 | 45 | |
| 17 | 10 | 50 | |
| 18 | 10 | 60 | |
| 19 | 10 | 70 | Low |

It has been found that the use of a combination or mixture of Tergitol 15-S-5 and 15S-9 in a 75 to 25 volumetric ratio, as employed in dye penetrant composition C, and as additive for desensitization, is particularly effective in producing excellent washability of excess penetrant from the part surface, while at the same time affording maximum entrappability of the penetrant solution in the cracks and defects open to the part surface.

In Table 2 above, it will be understood that the basic dye penetrant composition C can be replaced by the basic dye penetrant composition B of Table 1 above, containing the surfactant Plurafac A-24 as vehicle, and to which is added varying proportions of such Plurafac A-24 in the same progressively increasing proportions noted in the second column from the right in Table 2 above, to obtain dye penetrant compositions having varying sensitivity ranging from high plus to low, as noted in Table 2, dependent on the proportion of Plurafac A-24 additive vehicle incorporated into the basic dye penetrant composition.

Similarly, the basic dye penetrant composition C of Table 2 above can be replaced by dye penetrant composition A of Table 1, containing the single surfactant Tergitol 15-S-5, and adding additional progressively increasing proportions of the latter Tergitol surfactant to the basic dye penetrant composition A, as noted in Table 2, to again obtain dye penetrant compositions of controlled sensitivity ranging from high plus to low, as noted in Table 2.

Although generally the same oxyalkylated nonionic surfactant employed in the basic dye penetrant composition, is added to such composition to obtain the dye penetrant compositions of varying sensitivity noted above, if desired, a different oxyalkylated nonionic surfactant can be added to the basic dye penetrant composition, from the oxyalkylated surfactant employed therein. Thus, for example employing the basic dye penetrant composition A of Table 1 above, utilizing Tergitol 15-S-5 as vehicle, there can be added to such dye penetrant composition for desensitization thereof to obtain varying sensitivity dye penetrant formulations, Tergitol 15-S-9, or a combination of Tergitols 15-S-5 and 15-S-9.

All of the above noted dye penetrant compositions of varying sensitivity, such as the dye penetrant compositions C to 19 of Table 2 according to the invention, of varying sensitivity ranging from high plus to low, are all substantially water soluble and all have substantially the same water washability, but a different sensitivity or seeability, depending upon the amount of dilution of the basic dye penetrant.

Thus, the dye penetrant compositions of the invention, employing the above biodegradable nonionic oxyalkylated alcohol surfactants can be tailored to have varying degrees of sensitivity for detection of the smallest microcracks to gross cracks in a part surface by simply varying the amount of additional surfactant incorporated into the basic composition without regard to adjusting any additional components, and without changing or adversely affecting washability.

Where a developer composition is employed, any one of the three general types of developer compositions, namely, dry powder, wet aqueous (water-base) and wet non-aqueous (volatile solvent base) developer compositions can be employed. In each case, the developer composition contains a light colored powder, forming a coating which contrasts with the color of the dye in the penetrant and which acts as a wick or blotter, and causes liquid penetrant containing the dye, e.g. fluorescent dye, which was retained in the cracks or surface flaws, to be drawn up out of the surface defects by capillary action and to "bleed" through the powder.

Preferred developer compositions for use in conjunction with the dye penetrant compositions according to the invention, are those described in my U.S. Pat. No. 3,803,051, which is a dry powder developer containing fumed alumina, fumed silica, fumed titanium dioxide and talc, and in my U.S. Pat. No. 3,748,469, and which is a wet-non-aqueous developer composition consisting essentially of isopropyl alcohol, talc and glycol monobutyl ether. The descriptions of such developer compositions contained in the above patents are incorporated herein by reference.

In the method for detecting cracks and flaws in the surface of an object employing the dye penetrant compositions of varying sensitivity according to the invention, such dye penetrant is applied to the part surface in any suitable manner, as for example, by spraying or brushing. After application of the dye penetrant to the surface of the test part, the excess dye penetrant composition is readily removed from the object surface by water washing, e.g. by application of a water spray or sprayed mixture of air and water. The variable sensitivity dye penetrant compositions hereof, such as those containing the above noted Plurafacs and particularly those containing the above Tergitols 15-S-5 and 15-S-9, generally have excellent washability without removing dye penetrant from the cracks and defects on the part surface.

If desired, a developer composition of the types noted above can then be applied to the part surface followed be removal of excess developer, as by means of an air blast. The part is then viewed under suitable lighting conditions, employing black light or fluorescent illumination when the dye penetrant contains a fluorescent dye.

Illustrative examples of practice of the invention are set forth below.

EXAMPLE 1

A standard 2014 aluminum test panel having a wide range of cracks and defects disposed substantially uniformly over the panel, such cracks ranging from microcracks to medium and gross cracks, was used in the procedure below.

The single test panel was successively separately treated with the dye penetrant compositions C, 10, 14 and 19 of Table 2 above. The single test panel was washed and cleaned of each dye penetrant composition, after inspection, and before the next dye penetrant composition was applied to the panel.

In each case the fluorescent dye penetrant composition, commencing with dye penetrant composition C above, was applied as by spraying on the surface of the test panel, and excess dye penetrant composition on the test panel was removed by an air-water spray from the panel surface, without dislodging liquid dye penetrant from the surface cracks and thus entrapping the penetrant therein. The part was then dried by an air blast. The dye penetrant liquid removed from the part surface was biodegradable.

The penetrant treated surface of the test panel was then inspected under ultraviolet or fluorescent light, revealing fluorescent indications from the microcracks and cracks in the panel.

The use of compositions C, 10 and 14 resulted in comparative ratings of high plus, high and medium sensitivity for the respective compositions, as measured by the extent of crack detection on the panel, ranging from microcracks to medium and gross cracks for each of such compositions. Composition 19 was rated of low sensitivity as indicated by detection mostly of medium to gross cracks.

All of the above dye penetrant compositions had substantially the same good water washability although in each case, such dye penetrant composition contained the same amount of dye.

EXAMPLE 2

A set of tests was carried out similar to the procedure of Example 1 except that in place of dye penetrant composition C there was employed dye penetrant composition A containing only Tergitol 15-S-5, and there was added to such dye penetrant composition, additional amounts of Tergitol 15-S-5 in proportions corresponding to those set forth for composition 10, 14 and 19 of Table 2.

The results obtained were similar to those of Example 1, the dye penetrant compositions of this example having varying sensitivity ranging from high plus down to low, as in Example 1, with all of such dye penetrant compositions of varying sensitivity having substantially the same water washability and being biodegradable.

EXAMPLE 3

A set of tests was carried out similar to the procedure of Example 1 except that in place of dye penetrant composition C there was employed dye penetrant composition B containing Plurafac A-24, and there was added to such dye penetrant composition, Plurafac A-24 in proportions corresponding to those set forth for compositions 10, 14 and 19 of Table 2.

The results obtained were similar to those of Example 1, the dye penetrant compositions of this example having varying sensitivity also ranging from high plus down to low, as in Example 1, with all of such dye penetrant compositions of varying sensitivity having substantially the same water washability and being biodegradable.

EXAMPLE 4

The procedure of Example 1 was substantially followed except that after removal of excess dye penetrant composition from the part surface followed by air blasting for drying, the test panel in each of the tests was immersed in a dry powder developer having the following composition according to my above U.S. Pat. No. 3,083,051.

| COMPONENTS | PERCENT BY WEIGHT |
|---|---|
| Talc | 52 |
| Alumina | 35 |
| Silica | 4 |
| TiO$_2$ | 9 |

Excess developer composition was then carefully removed from the surfaces of the test panels by means of a gentle air blast.

The panels were then placed under black light (fluorescent) illumination and viewed.

Substantially the same results were obtained as in Example 1, with respect to varying sensitivity of the respective dye penetrant compositions as revealed by the detection of cracks ranging from microcracks to gross cracks, depending on the degree of dilution of the basic dye penetrant composition C with additional amounts of the mixture of Tergitol 15-S-5 and Tergitol 15-S-9.

From the foregoing, it is seen that the invention provides highly effective variable sensitivity biodegradable water washable dye penetrant compositions which can be readily formulated from a basic dye penetrant composition containing essentially oxyalkylated nonionic biodegradable surfactant as vehicle, by adding controlled amounts of such surfactant to the basic dye penetrant composition, while at the same time maintaining easy and good washability of the dye penetrant from the part, thus avoiding the requirement for mixing multiple components of conventional dye penetrant compositions for obtaining a predetermined dye sensitivity, and avoiding varying degrees of water washability of the resulting dye penetrant compositions resulting from such procedure.

Since various changes and modifications of the invention will occur to and can be made readily by those skilled in the art without departing from the invention concept, the invention is not to be taken as limited except by the scope of the appended claims.

What is claimed is:

1. A process for producing variable sensitivity water washable dye penetrant compositions which comprises preparing a basic dye penetrant composition which comprises (1) a biodegradable nonionic surfactant selected from the group consisting of (a) straight chain, primary, aliphatic oxyalkylated alcohols, wherein said alcohols can contain from 8 to 20 carbon atoms and the oxyalkyl groups are a mixtue of ethylene oxide and propylene oxide groups, and (b) ethoxyltes of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide and (2) a small amount of a dye soluble in said surfactant;

and incorporating predetermined additional amounts of said nonionic surfactant into said basic dye penetrant composition sufficient to decrease the sensitivity of said basic composition, the resulting desensitized dye penetrant compositions having substantially the same washability as said basic composition.

2. A process as defined in claim 1, said additional amounts of nonionic surfactants ranging from an amount which varies the sensitivity of the resulting dye penetrant composition from very high sensitivity to low sensitivity.

3. A process as defined in claim 1, said predetermined additional amount of nonionic surfactant contained in said variable sensitivity dye penetrant composition ranging from about 0.5 to about 100 parts, per 10 parts, by volume, of said basic dye penetrant composition.

4. A process as defined in claim 3, said dye being present in an amount ranging from about 0.1 to 15 parts, per 100 parts, by weight of said surfactant in said basic dye penetrant composition.

5. A process as defined in claim 3, wherein said surfactant (a) is a mixture of compounds having the formula:

R—O(A)H wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) is ethyoxylates of a mixture of alcohols having the formula:

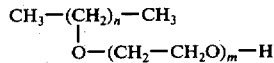

where $n$ is in the range from 9 to 13 and $m$ is an average of 3 to 12; and said dye is present in said basic dye penetrant composition in an amount ranging from about 0.1 to 15 parts, per 100 parts, by weight, of said surfactant, said composition being substantially non-flammable.

6. A process as defined in claim 5, wherein R in said surfactant (a) can have from 12 to 18 carbon atoms, and the total number of A groups can range from about 4 to about 14; and wherein in surfactant (b) the linear alkyl hydrophobic portion of said surfactant is a mixture of $C_{11}$ to $C_{15}$ linear chains, and the hydrophilic portion of said surfactant is a polyoxyethylene chain randomly attached to the linear alkyl hydrophobic chains through the ether linkage, and wherein said surfactant (b) is selected from the group consisting of said ethoxylates of said mixture of alcohols, wherein $n$ ranges from 9 to 13, and $m$ is an average of 3, 5, 7, 9 or 12.

7. A process as defined in claim 6, wherein said dye is a fluorescent dye.

8. A process as defined in claim 7, wherein said surfactant is said surfactant (b).

9. A process as defined in claim 8, said predetermined additional amount of a nonionic surfactant contained in said variable sensitivity dye penetrant composition ranging from about 1 to about 75 parts, per 10 parts, by volume, of said basic dye penetrant 10. A process as defined in claim 1, said predetermined additional amount of nonionic surfactant contained in said variable sensitivity dye penetrant composition ranging from about 1 to about 75 parts, per 10 parts, by volume, of said basic dye penetrant

* * * * *